United States Patent
Zhang et al.

(10) Patent No.: US 10,227,587 B2
(45) Date of Patent: Mar. 12, 2019

(54) METHOD FOR CONSTRUCTING A PLASMA DNA SEQUENCING LIBRARY

(71) Applicant: Berry Genomics Co., Ltd., Beijing (CN)

(72) Inventors: Jianguang Zhang, Beijing (CN); Yang Gao, Beijing (CN); Yanbin Shi, Beijing (CN); Di Chen, Beijing (CN); Feng Tian, Beijing (CN)

(73) Assignee: Berry Genomics Co., Ltd., Beijing (CN)

( * ) Notice: Subject to any disclaimer, the term of this patent is extended or adjusted under 35 U.S.C. 154(b) by 0 days.

(21) Appl. No.: 15/356,191

(22) Filed: Nov. 18, 2016

(65) Prior Publication Data
US 2018/0142235 A1  May 24, 2018

Related U.S. Application Data

(62) Division of application No. 14/345,671, filed as application No. PCT/CN2012/070162 on Jan. 10, 2012.

(51) Int. Cl.
  *C12N 15/10* (2006.01)
  *C12Q 1/68* (2018.01)
  *C12Q 1/6806* (2018.01)

(52) U.S. Cl.
  CPC ........... *C12N 15/1093* (2013.01); *C12Q 1/68* (2013.01); *C12Q 1/6806* (2013.01)

(58) Field of Classification Search
  CPC .............................. C12N 15/1093; C12Q 1/68
  USPC .......................................................... 506/10
  See application file for complete search history.

(56) References Cited

U.S. PATENT DOCUMENTS

| | | |
|---|---|---|
| 4,683,195 A | 6/1987 | Mullis et al. |
| 2003/0113737 A1 | 6/2003 | Pedersen |
| 2007/0093418 A1 | 4/2007 | Oliner et al. |
| 2009/0217399 A1 | 8/2009 | Stern et al. |
| 2010/0069250 A1 | 3/2010 | White, III et al. |
| 2014/0228256 A1 | 8/2014 | Zhang et al. |
| 2015/0307942 A1 | 10/2015 | Liu et al. |

FOREIGN PATENT DOCUMENTS

WO  WO 2009/126395 A1  10/2009

OTHER PUBLICATIONS

Paired-End Sequencing Sample Preparation Guide: For Research Use Only. (2009) Illumina, Part # 1005063 Rev. B:1-32.
Preparing Sample for ChIP Sequencing of DNC. (2007) Illumina, Part # 11257047, Rev. A:1-14.
Preparing Sample for Sequencing Genomic DNA. (2008) Illumina, Part # 1003806, Rev. B:1-18.
International Preliminary Report on Patentability corresponding to Chinese patent application No. PCT/CN2012/070162 dated Jul. 15, 2014.
International Search Report corresponding to Chinese patent application No. PCT/CN2012/070162 dated Oct. 25, 2012.
Office Action (Restriction Requirement) corresponding to U.S. Appl. No. 14/345,671 dated Oct. 7, 2015.
Office Action corresponding to U.S. Appl. No. 14/345,671 dated Nov. 23, 2015.
Office Action corresponding to U.S. Appl. No. 14/345,671 dated Jan. 27, 2017.
Office Action corresponding to U.S. Appl. No. 14/345,671 dated Jul. 28, 2017.

*Primary Examiner* — Karla A Dines
(74) *Attorney, Agent, or Firm* — Jenkins, Wilson, Taylor & Hunt, P.A.

(57) ABSTRACT

The disclosure relates to a method for constructing a plasma Deoxyribonucleic acid (DNA) sequencing library. The method includes: extracting a plasma DNA; making the plasma DNA ligate to a sequencing linker, and purifying a ligation product; performing Polymerase Chain Reaction (PCR) amplification for the purified ligation product, purifying the PCR amplification product, and obtaining the plasma DNA sequencing library, wherein, the method does not include the step of performing 5'-terminus phosphorylation for the plasma DNA. The kit provided by the disclosure includes: a reagent which ligates a plasma DNA to a sequencing linker, including the sequencing linker, a ligase and a ligation buffer; and reagents and instruments for purifying the ligation product; a reagent which performs PCR amplification for a purified ligation product, and reagents and instruments for purifying the PCR amplification product; wherein, the kit does not include the reagent which performs 5'-terminus phosphorylation for the plasma DNA.

11 Claims, 3 Drawing Sheets

METHOD FOR CONSTRUCTING A PLASMA DNA SEQUENCING LIBRARY

CROSS REFERENCE TO RELATED APPLICATIONS

This application is a divisional of U.S. patent application Ser. No. 14/345,671, filed Mar. 19, 2014, which itself is a National Stage Application of PCT/CN20102/070162, filed Jan. 10, 2012, the disclosure of each of which is incorporated herein by reference in its entirety.

TECHNICAL FIELD

The disclosure relates to a method for constructing a plasma Deoxyribonucleic acid (DNA) sequencing library, and in particular to a method for constructing a plasma DNA sequencing library for the second-generation high-throughput sequencing.

BACKGROUND

With the progress of science, the traditional Sanger sequencing cannot fully satisfy the needs of the research; the genome sequencing needs a sequencing technology which has lower cost, higher throughput and faster speed, so the second-generation sequencing technology is emerged at the right moment. The core idea of the second-generation sequencing technology is sequencing by synthesis, namely, to determine the DNA sequence by catching the mark of the newly-synthesized end; the existing technical platform mainly includes Roche/454 FLX, Illumina/Solexa Genome Analyzer and Applied Biosystems SOLID system and the like. Taking Illumina product as an example, the GAII reading length has been developed to be 100 bases at present from 36 bases in 2008, and the throughput has been developed to be 240M reads/run at present from 48M reads/run in 2008, the sequencing capacity has been improved by 14 times. By now, each run of HiSeq 2000 can achieve 3 human genomes and 30× coverage sequencing throughput, approximately 300 G/run data, and the processing time on an equipment has been reduced to 30 min. As the second-generation sequencing technology becomes more mature, it is rapidly developed to be applied in clinical research. Studies show that genetic health condition of a fetus can be judged by sequencing the maternal plasma DNA; and the early cancer screening can be performed by sequencing the plasma DNA of test people, thus the second-generation sequencing technology has a strong prospect for application.

The plasma DNA is also called circulating DNA, which is the extracellular DNA in the blood, and of which the length is approximately tens to hundreds of nucleotides; the plasma DNA can exist in the form of DNA-protein complex, and also can be free DNA fragments. Under normal circumstances, the plasma DNA derives from the DNA which is released by a small amount of aging dead cells. In a healthy state, the generation and removal of the circulating DNA are in a dynamic balancing state, and are maintained at a relatively constant low level. The circulating DNA can reflect the status of the cell metabolism of the human body, which is an important indicator of health evaluation. The change of quantity and quality of the peripheral blood circulating DNA have a close relationship with various diseases (including tumour, severe composite trauma, organ transplantation, pregnancy-related diseases, infectious diseases, organ failure and the like); as a non-invasive detection indicator, the circulating DNA can possibly become an important molecular marker for performing early diagnosis, illness monitoring, therapeutic effect evaluation and prognosis evaluation of some diseases.

Since the presence of fetal DNA in maternal plasma was validated[3], non-invasive prenatal diagnosis and detection of fetal chromosomal abnormalities has become a major research subject. In 2007, Professor Lu Yuming and his colleagues proved that the ratio of mutation site of the placental specific gene 4 in maternal plasma Messenger Ribonucleic Acid (RNA) (mRNA) could be used to judge whether the fetus has chromosome 21# which was a triploid[4]. The ratio of mutation site is also used for judging whether the chromosome 18# is triploid[5]. The limitation of these methods above is that the mutation site is not common in the crowd, therefore, these methods are only suitable for a part of crowd. During the same period, digital Polymerase Chain Reaction (PCR) (dPCR) is used for detecting the fetus with chromosomal triploidy[6], [7]. The advantage of the dPCR is that it does not depend on any mutation site; however, the accuracy of dPCR is insufficient, and also requires a large amount of blood samples, which increases the difficulty in sampling.

In recent years, the high-throughput sequencing technologies which are rapidly developed have solved the problems above. These technologies include Genome Analyzer[8] of Illumina Company, SOLiD[9] of Life Technologies Company, and Heliscope[10] of Helicos Company, by which hundreds of millions or even billions of sequences can be detected for once. When detecting the DNA in maternal plasma by these technologies, the change of the chromosome number of a trace amount of fetal DNA in the plasma can be detected[11], [12], [13]. But because of high sequencing cost, the technologies have not yet been widespread used at present. Meanwhile, the way of detecting the change of local copy number of the embryonic chromosomes from the maternal blood is an unsolved problem. There are some advantages to detect the change of copy number of the fetal chromosomes from maternal plasma by the high-throughput sequencing; however, the high-throughput sequencing is expensive and cannot be popularized. Moreover, the Coefficient of Variation (CV) of sequencing is high, and the accuracy and stability of detection also need to be improved. And the CV of sequencing also determines that the method is only suitable for a few chromosomes, such as chromosome 21# and chromosome 18#, but unsuitable for detecting the change of partial copy number of the chromosomes at present.

The improvement of the sequencing efficiency and the popularization of multi-sample mixed sequencing demand higher efficiency in preparing samples, particularly in preparing large number of clinical samples; however, the present method of preparing clinical plasma sample pull up to the improvement of the sequencing capacity. Therefore, the efficiency and cost in preparing clinical plasma DNA samples for the second-generation high-throughput sequencing have become the key for high-throughput sequencing to be popular.

Figure 1:
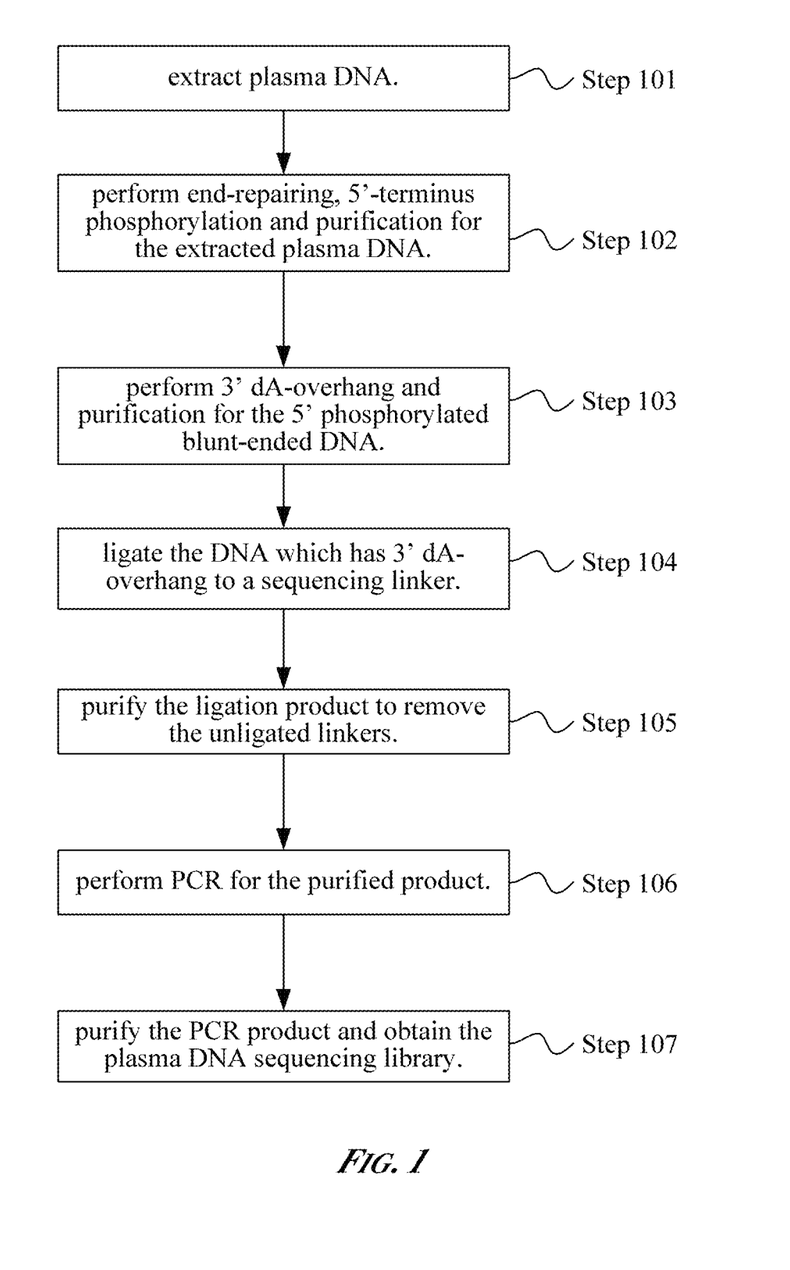
FIG. 1 shows a method for constructing a second-generation high-throughput plasma DNA sequencing library which is normally adopted in the prior art.

Essentially, the process of preparing plasma DNA samples for the second-generation high-throughput sequencing is inserting the DNA which satisfies the sequencing length into the existing sequencing vector, namely, ligating the known sequencing linker on two ends of the DNA to be sequenced. At present, the construction of the plasma DNA library mainly includes: firstly performing end-repairing and 5'-terminus phosphorylation for the extracted plasma DNA, and then performing the main steps, such as dA-overhang, linker ligation and PCR and the like (FIG. 1), wherein, the purification step needs to be implemented in each of the steps above. Such construction method of the plasma DNA sequencing library totally needs 6 main enzymes, 4 enzyme reaction systems, and cleaning and purifying for four times; therefore, it is high in cost and complex in operation, and requires more in operating capacity of the molecular biology for experimenter, and it is difficult to process multiple samples synchronously.

SUMMARY

In view of the above problems existing in the constructing process of the clinical plasma DNA sequencing library, the inventor invents a new simpler and faster method for constructing the clinical plasma DNA sequencing library, which is suitable for various second-generation sequencing platforms, including but not limited to the sequencing platforms such as Roche/454 FLX, Illumina/Solexa Genome Analyzer, Applied Biosystems SOLID system, Life Technologies Ion Torrent and the like.

The disclosure is based on the following facts: the inventor finds that the terminus of DNA in plasma includes monophosphate group, the 5'-terminus phosphorylation referred in the end-filling step of the existing experimental flow is not necessary, thus T4 Polynucleotide Kinase (T4 PNK) and Adenosine Triphosphate (ATP) need not to be used. Based on the findings above, the inventor also finds that without using T4 PNK and ATP, the three-step reactions of end-filling, dA-overhang and sequencing linker ligation in the existing experimental flow cannot necessarily be performed in three reaction systems factually, depending on the selection of enzyme adopted for dA-overhang, but can be performed only in two reaction systems or even only in one independent reaction system without purification steps. Further, the inventor also finds that the DNA library which satisfies the high-throughput sequencing requirements also can be obtained by using a single-strand sequencing linker instead of the double-strand sequencing linker, directly ligating the linker to an extracted plasma DNA, and then performing purification, PCR amplification and the like, without end-filling and dA-overhang.

Based on the above findings, according to one aspect, the disclosure provides a method for constructing a plasma DNA sequencing library; which includes the steps as follows: extracting a plasma DNA; making the plasma DNA ligate to a sequencing linker, and purifying a ligation product; performing PCR amplification for a purified ligation product, purifying a PCR amplification product, and obtaining the plasma DNA sequencing library; wherein, one important characteristic of the disclosure is that the method does not include the step of performing 5'-terminus phosphorylation for the plasma DNA.

Preferably, according to the method of the disclosure, the ligation of the plasma DNA and the sequencing linker is performed by adopting one or more ligases selected from the group consisting of: a T4 DNA ligase, a T4 RNA ligase and a T7 DNA ligase.

According to the method of the disclosure, in some embodiments, the sequencing linker is a single-strand sequencing linker; and in other embodiments, the sequencing linker is a double-strand sequencing linker.

In the case that the sequencing linker is the double-strand sequencing linker, in one embodiment, the method of the disclosure further includes the step of: after extracting the plasma DNA, and before ligating the plasma DNA to the sequencing linker, performing dA-overhang for the extracted plasma DNA, and purifying the plasma DNA with dA-overhang. Preferably, the dA-overhang adopts klenow ex-enzyme, or Taq enzyme, or the combination of klenow ex-enzyme and Taq enzyme. Alternatively, the dA-overhang and the ligation of the sequencing linker can be performed in one reaction system, namely, the purification can be omitted after performing dA-overhang, and the ligation of the sequencing linker is directly performed, wherein the dA-overhang adopts the Taq enzyme.

In the case that the sequencing linker is the double-strand sequencing linker, in another embodiment, the method of the disclosure further includes the steps of: after extracting the plasma DNA, and before ligating the plasma DNA to the sequencing linker, performing end-filling and dA-overhang for an extracted plasma DNA. Wherein, the end-filling and dA-overhang may be performed in two reaction systems, namely, the step of dA-overhang is performed after the step of the end-filling and the purification; and preferably, the end-filling and dA-overhang are performed in one reaction system, the plasma DNA is purified after performing the end-filling and dA-overhang, wherein, the T4 DNA polymerase is adopted in the step of end-filling, and the Taq enzyme is adopted in the step of dA-overhang; or more preferably, the end-filling and the dA-overhang, and the ligation between the plasma DNA and the sequencing linker are performed in one reaction system, wherein, the T4 DNA polymerase is adopted in the step of the end-filling, and the Taq enzyme is adopted in the step of dA-overhang.

According to another aspect, the disclosure provides a kit for constructing a plasma DNA sequencing library; the kit includes: a reagent which ligates a plasma DNA to a sequencing linker, including the sequencing linker, a ligase and a ligation buffer; and reagents and instruments used for purifying a ligation product; a reagent which performs PCR amplification for a purified ligation product, and reagents and instruments for purifying the PCR amplification product; wherein, one important characteristic of the kit of the disclosure is that the kit does not include the reagent which performs 5'-terminus phosphorylation for the plasma DNA.

Preferably, according to the kit of the disclosure, the ligase is selected from the group consisting of: T4 DNA ligase, T4 RNA ligase and T7 DNA ligase.

According to the kit of the disclosure, in some embodiments, the sequencing linker is a single-strand sequencing linker; and in other embodiments, the sequencing linker is a double-strand sequencing linker.

In the case that the sequencing linker is the double-strand sequencing linker, in one embodiment, the kit of the disclosure further includes: a reagent which performs dA-overhang for the extracted plasma DNA, including Deoxyadenosine Triphosphate (dATP), an enzyme for dA-overhang, a buffer for dA-overhang; and reagents and instruments used for purifying the plasma DNA with dA-overhang. Preferably, the enzyme used for dA-overhang is klenow ex-enzyme, or Taq enzyme, or the combination of klenow ex-enzyme and Taq enzyme.

In the case that the sequencing linker is the double-strand sequencing linker, in another embodiment, the kit of the disclosure further includes: a regent which respectively performs end-filling and dA-overhang for the extracted plasma DNA, including an enzyme for end-filling, Diethyl-Nitrophenyl Thiophosphate (dNTP), a buffer for end-filling, Deoxyadenosine Triphosphate (dATP), an enzyme for dA-overhang, and a buffer for dA-overhang; and the reagents and instruments used for purifying an end-filled and dA-overhanged plasma DNA.

In the case that the sequencing linker is the double-strand sequencing linker, in another embodiment, the kit of the disclosure further includes: a regent which performs end-filling and dA-overhang for the extracted plasma DNA, including an enzyme for end-filling, dNTP, an buffer for end-filling, dATP, an enzyme for dA-overhang, and a buffer for dA-overhang; and the reagents and instruments used for purifying an end-filled and dA-overhanged plasma DNA; wherein, the end-filling and dA-overhang are performed in one reaction system, and the T4 DNA polymerase is adopted for end-filling; and the Taq enzyme is adopted for dA-overhang.

In the case that the sequencing linker is the double-strand sequencing linker, in another embodiment, the kit of the disclosure further includes: a regent which performs end-filling and dA-overhang for the extracted plasma DNA, including an enzyme for end-filling, dNTP, a buffer for end-filling, dATP, an enzyme for dA-overhang, and a buffer for dA-overhang; wherein, the end-filling and dA-overhang, and the ligation between the plasma DNA and the sequencing linker are performed in one reaction system; the T4 DNA polymerase is adopted for end-filling; and the Taq enzyme is adopted for dA-overhang.

Based on the unexpected discovery that the terminus of DNA in plasma includes a monophosphate group, the disclosure omits the 5'-terminus phosphorylation which is necessary in the existing construction method of the plasma DNA sequencing library, and does not use the T4 PNK and the ATP; furthermore, on this basis, the disclosure performs the step of dA-overhang by using the normal Taq polymerase to replace the klenow ex-enzyme, thus the buffers of various reactions can be compatible; the steps of end-filling, dA-overhang and linker ligation can be performed in two or only one reaction system; additionally, the disclosure adopts the double-strand sequencing linker instead of the single-strand sequencing linker to perform the ligation of the linker without the end-filling and dA-overhang steps in the prior art. Thus, the disclosure greatly simplifies the construction of the plasma DNA sequencing library and the experimental procedures, makes the cost of construction of the plasma sample library more lower, the efficiency more higher and the speed more faster, so it is convenient for large-scale application.

BRIEF DESCRIPTION OF THE DRAWINGS

FIG. 3a and FIG. 3b show the electrophoresis results of the plasma DNA sequencing library which is constructed according to the method of the disclosure.

DETAILED DESCRIPTION

As mentioned above, the construction of the plasma DNA library suitable for the second-generation high-throughput sequencing platform at present mainly includes the steps as follows (referring to FIG. 1): extracting a plasma DNA (Step 101)—performing end-repairing (filling), 5'-terminus phosphorylation and purification for a extracted plasma DNA (Step 102)—performing 3' dA-overhang and purification for the 5' phosphorylated blunt-ended DNA fragments (Step 103)—ligating the DNA with 3' dA-overhang to the sequencing linker (Step 104)—purifying a ligation product in order to remove the unligated linker (Step 105)—performing PCR for a purified product (Step 106)—purifying a PCR product, and obtaining the plasma DNA sequencing library (Step 107). Wherein, the purification step needs to be performed almost in each of the steps. Therefore, the construction method of the second-generation plasma DNA sequencing library totally requires 6 main enzymes, 4 enzyme reaction systems, and cleaning and purifying for 4 times; thus this method has higher cost and complicated operation, requires higher operating capability for experimenter in molecular biology, and it is hard to process multiple samples synchronously.

Via repeated experiments, the inventor unexpectedly finds that the terminus of DNA in the plasma includes a monophosphate group, and the 5'-terminus phosphorylation referred in the end-filling step of the existing experimental flow is unnecessary, thus the T4 PNK and ATP can be omitted in the construction of the plasma DNA sequencing library; therefore, one of the important characteristics of constructing the plasma DNA sequencing library in the disclosure is excluding the step of 5'-terminus phosphorylation.

On this basis, the inventor also finds that, under the condition of not using the T4 PNK and the ATP, the end-filling, dA-overhang and the ligation of sequencing linker in the existing experimental flow cannot necessarily be performed in three reaction systems, by depending on the selection of enzyme adopted in dA-overhang, but can be performed only in two reaction systems, or even only in one independent reaction system, without purification step thereamong.

In addition, the inventor also finds that the steps of end-filling and dA-overhang can be omitted by adopting a single-strand sequencing linker instead of the double-strand sequencing linker; the DNA library which satisfies the high-throughput sequencing requirements also can be obtained by directly ligating the extracted plasma DNA to the linker, and then performing the purification and PCR amplification steps and the like.

Figure 2:
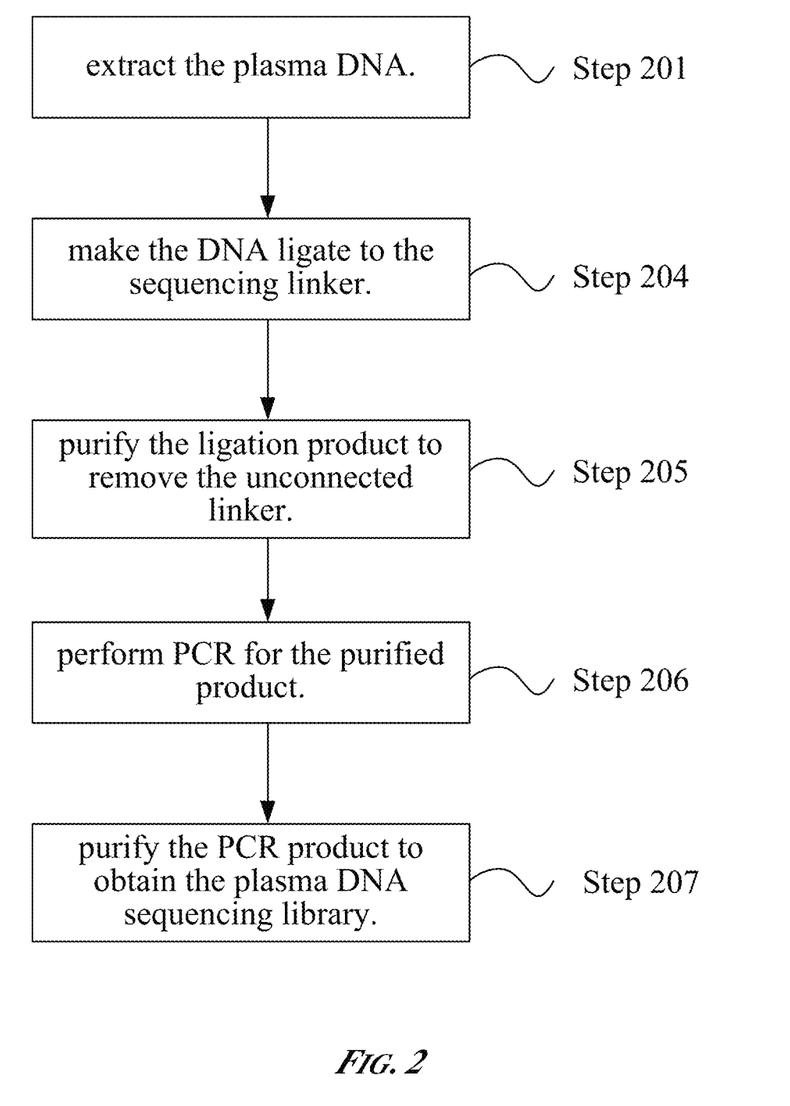
FIG. 2 shows a method for constructing a second-generation high-throughput plasma DNA sequencing library according to one embodiment of the disclosure.

FIG. 2 shows a method for constructing a second-generation high-throughput plasma DNA sequencing library according to one embodiment of the disclosure, mainly including the steps of: extracting the plasma DNA (Step 201)—ligating the DNA to the sequencing linker (Step 204)—purifying a ligation product in order to remove the unligated linker (Step 205)—performing PCR for a purified product (Step 206)—purifying a PCR product, and obtaining a plasma DNA sequencing library (Step 207). According to another embodiment of the disclosure, between the Step 201 and the Step 204, the method further includes: Step 202—performing end-repairing and 5'-terminus phosphorylation for a extracted plasma DNA, and Step 203—performing 3' dA-overhang for the 5' phosphorylated blunt-ended DNA fragments (not shown in the figures); the Step 202 and Step 203 can be performed in the same reaction system; or the Step 202, Step 203 and Step 204 can be performed in the same reaction system.

Compared with the method for constructing the plasma DNA sequencing library in the prior art, the method of the disclosure obviously simplifies the construction flow of the plasma DNA sequencing library, simplifies the experimental procedures, makes the construction of the plasma sample library have lower cost, higher efficiency and faster speed, and is convenient for large-scale application.

The disclosure is described as below with reference to drawings and in conjunction with embodiments in details. It should be noted that, the drawings and embodiments in the disclosure are only used for the exemplification purposes for those skilled in the art, not forming any limitation to the disclosure. The embodiments in the application and the characteristics in the embodiments can be mutually combined without contradiction.

Embodiment: A Method of Constructing Plasma DNA Sequencing Library that Suitable for Next-Generation High-Throughput Sequencing According to the Disclosure Embodiment 1

The method for constructing a plasma DNA sequencing library in the embodiment 1 mainly includes the steps as follows:

(1) extracting plasma DNA: this step can be performed by using any method and reagent suitable for extracting the plasma DNA which are known by those skilled in the art.
(2) performing end-filling, and then cleaning and purifying the products: this step can be performed by using any method and reagent suitable for end-filling and the following step of cleaning and purification which are known by those skilled in the art. For example, the T4 DNA polymerase, and the Klenow can be used as the enzyme for end-filling.
(3) performing dA-overhang, and then cleaning and purifying the products: this step can be performed by using any method and reagent suitable for performing dA-overhang and then cleaning and purifying the products which are known by those skilled in the art. For example, a base can be over-hanged from the double-strand ends by the product of the former step under the effect of klenow ex-(New England Biolabs) (which is an improved klenow enzyme, of which 3'-5' exonuclease is inactivity).
(4) ligating the sequencing linker, and then cleaning and purifying the products: this step can be performed by using any method and reagent suitable for ligating the linker and then cleaning and purifying the products which are known by those skilled in the art. For example, the dA-overhang and the double-strand sequencing linker can be connected under the effect of T4 DNA ligase, T4 RNA ligase, T7 DNA ligase, or the combination of two or more thereof. Wherein, the sequencing linker can be commercially available or self-synthesized.
(5) performing PCR amplification for the cleaning products obtained in the former step, and then cleaning and purifying the products: as the PCR reaction is very mature in this field, the selection of the primers and polymerases of the PCR reaction, and the design of the PCR reaction circulation are also within the capacities of those skilled in the art.

In addition, before the high-throughput sequencing, the following operations need to be performed for the library above:

(6) using quantitative tools, such as nano drop (nano drop technology Co., Ltd.), Bioanalyser 2100 (Agilent), Qubit (Life Technologies) or qPCR to quantify the sequencing library;
(7) mixing an equal amount of different samples according to the arrangement of channels of equipment and the difference of the tag sequence;
(8) samples processed by equipment.

One Embodiment for Sequencing the Plasma DNA Sample According to the Method of the Embodiment 1 of the Disclosure is Shown Below Step 1: extracting approximate 5 ng plasma DNA.

Step 2: preparing the end-filling reaction mixture as shown in Table 1, and incubating at 20 degrees centigrade for 30 min; purifying the DNA samples by a purification column, and eluting the samples with 42 μl of sterile dH$_2$O or elution buffer. Wherein, the elution buffer adopted in the disclosure is 10 mM Tris-Cl, pH 8.0, however, the elution buffer suitable for the disclosure is not limited thereby.

TABLE 1

| Plasma DNA solution | 40.5 μl |
| --- | --- |
| T4 DNA polymerase buffer (10X) | 5 μl |
| 10 mM dNTP mixture | 2 μl |
| T4 DNA polymerase | 2 μl |
| Klenow enzyme | 0.5 μl |
| Sterile H$_2$O | 0 μl |
| Total volume | 50 μl |

Step 3: preparing the reaction mixture which is used for overhanging polyadenylation tail at the 3'-terminus as shown in Table 2, and incubating at 37 degrees centigrade for 30 min; purifying the DNA samples by a purification column, and eluting the samples with 25 μl of sterile dH$_2$O or elution buffer.

TABLE 2

| Blunt-ended DNA | 32 μl |
| --- | --- |
| Klenow reaction buffer (10X) | 5 μl |
| dATP solution | 10 μl |
| klenow ex-(3'-5' exonuclease activity deletion) | 3 μl |
| Sterile H$_2$O | 0 μl |
| Total volume | 50 μl |

Step 4: preparing the reaction mixture for ligating the DNA fragment to the sequencing linker as shown in Table 3, and incubating at 20 degrees centigrade for 15 min; purifying and recycling the DNA samples on a Qiagen column, and eluting the samples with 25 μl of sterile dH$_2$O or elution buffer.

TABLE 3

| End-filled, dA-tail DNA | 33 μl |
| --- | --- |
| Fast ligation reaction buffer (5X) | 10 μl |
| 5 μM DNA linker | 2 μl |
| Fast T4 DNA ligase (NEB) | 5 μl |
| Total volume | 50 μl |

Step 5: preparing the PCR reaction mixture as shown in Table 4, enriching the linker-modified DNA fragments by PCR; extracting the DNA samples by a Qiagen column, and eluting the samples with 25 μl of sterile dH$_2$O or elution buffer.

TABLE 4

| DNA | 12.5 μl |
| --- | --- |
| Phusion DNA polymerase (Phusion DNA polymerase mixture) | 25 μl |
| PCR primer mixture | 2 μl |
| Ultrapure water | 10.5 μl |
| Total volume | 50 μl |

The PCR reaction program is: a. 98 degrees centigrade for 30 s—b. 18 circulations as below: 98 degrees centigrade for 10 s, 65 degrees centigrade for 30 s, 72 degrees centigrade for 30 s—c. 72 degrees centigrade for 5 min—d. Maintaining at 4 degrees centigrade.

Step 6: quantifying and mixing the libraries: taking 1 μl of library to quantify by Qubit; mixing an equal amount of the sample libraries with different linkers in the same channel according to the channel arrangement; and taking 1 μl of library to quantify by Qubit again.

Step 7: sequencing by equipment: diluting the first-end sequencing primer, the tag primer and the second-end sequencing primer to 100 μM; operating the equipment according to the Illumina GAIIx operating instructions. Alternatively, the double-end sequencing can be performed, and the single-end sequencing also can be performed, the second-end sequencing primer can be omitted when performing the single-end sequencing.

Figure 3A:
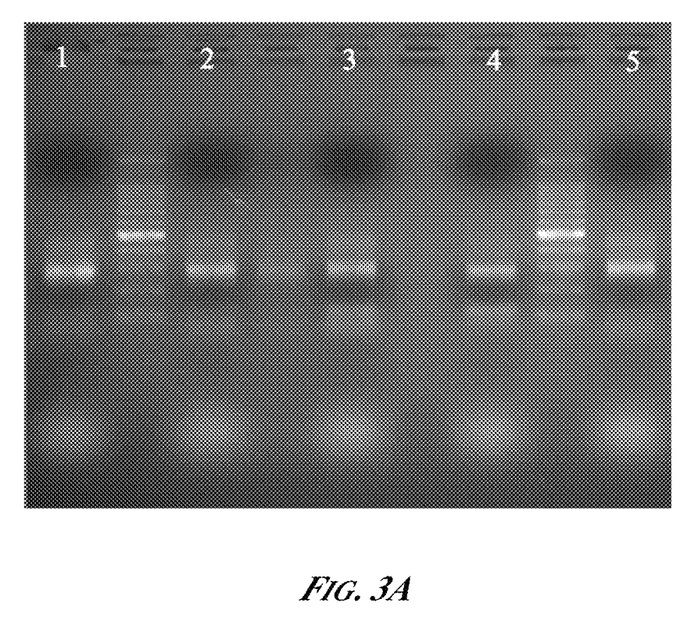
FIG. 3a shows the electrophoresis results of the plasma DNA sequencing library which is constructed according to embodiments 1-4, wherein, the electrophoresis path 1 is the plasma DNA sequencing library which is constructed as a comparison according to the existing method; and the electrophoresis paths 2-5 are respectively the plasma DNA sequencing libraries which are constructed according to the embodiments 1-4.

Results: the result of sequencing by equipment shows that the plasma DNA sequencing library constructed according to the embodiment 1 of the disclosure can satisfy the design requirements of the second-generation high-throughput sequencing. By electrophoresis experiments, it finds that the constructed sequencing library has similar bands (as shown in FIG. 3a and the electrophoresis path 2) to the DNA library constructed by a traditional method.

Embodiment 2

The method for constructing a plasma DNA sequencing library of the embodiment 2 is basically similar to the embodiment 1; the difference is that, the embodiment 2 does not include the end-filling step, and directly performs dA-overhang and purification for the extracted plasma DNA.

One Embodiment of Sequencing the Plasma DNA Samples by using the Method According to the Embodiment 2 of the Disclosure is Shown as Below Step 1: extracting approximate 5 ng of the plasma DNA.

Step 2: preparing the reaction mixture as shown in Table 5, and incubating at 37 degrees centigrade for 30 min, so as to overhang polyadenylation tail at the 3'-terminus of the DNA fragment; purifying the DNA samples by a purification column, and eluting the samples with 25 μl of sterile dH$_2$O or elution buffer.

TABLE 5

| Blunt-ended DNA | 32 μl |
| Klenow reaction buffer (10X) | 5 μl |
| klenow ex- (3'-5' exonuclease inactivity) | 3 μl |
| dATP solution | 10 μl |
| Sterile H$_2$O | 0 μl |
| Total volume | 50 μl |

Step 3: preparing the reaction mixture as shown in Table 6, and incubating at 20 degrees centigrade for 15 min; ligating a double-strand linker for the DNA fragment; purifying the DNA samples by a Qiagen column, and eluting the samples with 25 μl of sterile dH$_2$O or elution buffer.

TABLE 6

| Blunt-ended, dA-tail DNA | 33 μl |
| Fast ligation reaction buffer (5X) | 10 μl |
| 5 μM DNA linker | 2 μl |
| Fast T4 DNA ligase (NEB) | 5 μl |
| Total volume | 50 μl |

Step 4: preparing the reaction mixture as shown in Table 7, and enriching the linker-modified DNA fragments by PCR; extracting the DNA samples by a Qiagen column, and eluting the samples with 25 μl of sterile dH$_2$O or elution buffer.

TABLE 7

| DNA | 12.5 μl |
| Phusion DNA polymerase (Phusion DNA polymerase mixture) | 25 μl |
| PCR primer mixture | 2 μl |
| Ultrapure water | 10.5 μl |
| Total volume | 50 μl |

The PCR reaction program is: a. 98 degrees centigrade for 30 s—b. 18 circulations as below: 98 degrees centigrade for 10 s, 65 degrees centigrade for 30 s, 72 degrees centigrade for 30 s—c. 72 degrees centigrade for 5 min—d. Maintaining at 4 degrees centigrade.

Step 5: quantifying and mixing the libraries: taking 1 μl of library to quantify by Qubit; mixing an equal amount of the sample libraries with different linkers in the same channel according to the channel arrangement; and taking 1 μl of library to quantify by Qubit again.

Step 6: sequencing by equipment: diluting the first-end sequencing primer, the tag primer and the second-end sequencing primer to 100 μM; operating the equipment according to the Illumina GAIIx operating instructions. Alternatively, the double-end sequencing can be performed, and the single-end sequencing also can be performed, the second-end sequencing primer can be omitted when performing the single-end sequencing.

Results: the result of sequencing by equipment shows that the plasma DNA sequencing library constructed according to the embodiment 2 of the disclosure can satisfy the design requirements of the second-generation high-throughput sequencing. By electrophoresis experiments, it finds that the constructed sequencing library has similar bands (as shown in FIG. 3a, the electrophoresis path 3) to the DNA library constructed by a traditional method.

Embodiment 3

The method for constructing a plasma DNA sequencing library of the embodiment 3 is basically similar to the embodiment 1; and the difference is that, in the embodiment 3, the end-filling and the dA-overhang are performed in one reaction system, the step of cleaning and purifying is omitted between the end-filling and the dA-overhang, wherein the dA-overhang uses the ordinary Taq enzyme instead of the commonly-used Klenow ex-enzyme, in order to make the buffer systems of the two reactions be compatible.

One Embodiment of Sequencing the Plasma DNA Samples by using the Method According to the Embodiment 3 of the Disclosure is Shown as Below Step 1: extracting approximate 5 ng of the plasma DNA.

Step 2: preparing the reaction mixture as shown in Table 8, and incubating at 37 degrees centigrade for 20 min (end-filling), and then incubating at 72 degrees centigrade for 20 min (dA-overhang), so as to perform the end-filling and dA-overhang in one reaction system; purifying the DNA samples by a purification column, and eluting the samples with 42 μl of sterile dH$_2$O or elution buffer. The temperature and time of end-filling and dA-overhang can be different according to the composition of different reaction mixtures suitable for different design requirements.

TABLE 8

| | |
|---|---|
| Plasma DNA solution | 40.5 μl |
| T4 DNA polymerase buffer (10X) | 5 μl |
| 10 mM dNTP mixture | 2 μl |
| T4 DNA polymerase | 2 μl |
| Taq polymerase | 0.5 μl |
| Sterile H$_2$O | 0 μl |
| Total volume | 50 μl |

Step 3: preparing the reaction mixture as shown in Table 9, and incubating at 20 degrees centigrade for 15 min; ligating linker for the DNA fragments; purifying and recycling the DNA samples by a Qiagen column, and eluting the samples with 25 μl of sterile dH$_2$O or elution buffer.

TABLE 9

| | |
|---|---|
| End-filled, dA-tail DNA | 33 μl |
| Fast ligation reaction buffer (5X) | 10 μl |
| 5 μM DNA linker | 2 μl |
| Fast T4 DNA ligase (NEB) | 5 μl |
| Total volume | 50 μl |

Step 4: preparing the reaction mixture as shown in Table 10, enriching the linker-modified DNA fragments by PCR, extracting the DNA samples by a Qiagen column, and eluting the samples with 25 μl of sterile dH$_2$O or elution buffer.

TABLE 10

| | |
|---|---|
| DNA | 12.5 μl |
| Phusion DNA polymerase (Phusion DNA polymerase mixture) | 25 μl |
| PCR primer mixture | 2 μl |
| Ultrapure water | 10.5 μl |
| Total volume | 50 μl |

The PCR reaction program is: a. 98 degrees centigrade for 30 s—b. 18 circulations as below: 98 degrees centigrade for 10 s, 65 degrees centigrade for 30 s, 72 degrees centigrade for 30 s—c. 72 degrees centigrade for 5 min—d. Maintaining at 4 degrees centigrade.

Step 5: quantifying and mixing the libraries: taking 1 μl of library to quantify by Qubit; an equal amount of mixing the sample libraries with different linkers in the same channel according to the channel arrangement; and taking 1 μl of library to quantify by Qubit again.

Step 6: sequencing by equipment: diluting the first-end sequencing primer, the tag primer and the second-end sequencing primer to 100 μM; operating the equipment according to the Illumina GAIIx operating instructions. Alternatively, the double-end sequencing can be performed, and the single-end sequencing also can be performed, the second-end sequencing primer is saved when performing the single-end sequencing.

Results: the result of sequencing verification shows that the plasma DNA sequencing library constructed according to the embodiment 3 of the disclosure can satisfy the design requirements of the second-generation high-throughput sequencing. By electrophoresis experiments, it finds that the constructed sequencing library has similar bands (as shown in FIG. 3a, the electrophoresis path 4) to the DNA library constructed by a traditional method.

Embodiment 4

The method for constructing a plasma DNA sequencing library of the embodiment 4 is basically similar to the embodiment 1, and the difference is that, in the embodiment 4, the end-filling, the dA-overhang and the ligation of the sequencing linker are performed in one reaction system, the step of cleaning and purifying is omitted between the end-filling and the dA-overhang, and between the dA-overhang and the ligation of the sequencing linker, wherein the dA-overhang uses the ordinary Taq enzyme instead of the commonly-used Klenow ex-enzyme, in order to make the buffer systems of the three reactions be compatible.

One Embodiment of Sequencing the Plasma DNA Samples by using the Method According to the Embodiment 4 of the Disclosure is Shown as Below Step 1: extracting approximate 5 ng of the plasma DNA.

Step 2: preparing the reaction mixture as shown in Table 11, incubating at 37 degrees centigrade for 20 min (end-filling), and then incubating at 72 degrees for 20 min (dA-overhang), so as to perform the end-filling and dA-overhang; the purification step is not performed here.

TABLE 11

| | |
|---|---|
| Plasma DNA solution | 40.5 μl |
| T4 DNA polymerase buffer (10X) | 5 μl |
| 10 mM dNTP mixture | 2 μl |
| T4 DNA polmyerase | 2 μl |
| Taq polymerase | 0.5 μl |
| Sterile H$_2$O | 0 μl |
| Total volume | 50 μl |

Step 3: adding extra reaction agent into the former reaction solution to prepare the reaction mixture as shown in Table 12, incubating at 20 degrees centigrade for 15 min, in order to ligate sequencing linker to the DNA fragments; purifying and recycling the DNA samples by a Qiagen column, and eluting the samples with 25 μl of sterile dH$_2$O or elution buffer.

TABLE 12

| | |
|---|---|
| Reaction solution of the former step | 50 μl |
| Fast ligation reaction buffer (10X) | 10 μl |
| 5 μM DNA linker | 2 μl |
| Fast T4 DNA ligase (NEB) | 5 μl |
| Total volume | 100 μl |

Step 4: preparing the reaction mixture as shown in Table 13, enriching the linker-modified DNA fragments by PCR, extracting the DNA samples by a Qiagen column, and eluting the samples with 25 μl of sterile dH$_2$O or elution buffer.

TABLE 13

| | |
|---|---|
| DNA | 12.5 μl |
| Phusion DNA polymerase (Phusion DNA polymerase mixture) | 25 μl |
| PCR primer mixture | 2 μl |
| Ultrapure water | 10.5 μl |
| Total volume | 50 μl |

The PCR reaction program is: a. 98 degrees centigrade for 30 s—b. 18 circulations as below: 98 degrees centigrade for 10 s, 65 degrees centigrade for 30 s, 72 degrees centigrade for 30 s—c. 72 degrees centigrade for 5 min—d. Maintaining at 4 degrees centigrade.

Step 5: quantifying and mixing the libraries: taking 1 μl of library to quantify by Qubit; an equal amount of mixing the sample libraries with different linkers in the same channel according to the channel arrangement; and taking 1 μl of library to quantify by Qubit again.

Step 6: sequencing by equipment: diluting the first-end sequencing primer, the tag primer and the second-end sequencing primer to 100 μM; operating the equipment according to the Illumina GAIIx operating instructions. Alternatively, the double-end sequencing can be performed, and the single-end sequencing also can be performed, the second-end sequencing primer is saved when performing the single-end sequencing.

Results: the result of sequencing by equipment shows that the plasma DNA sequencing library constructed according to the embodiment 3 of the disclosure can satisfy the design requirements of the second-generation high-throughput sequencing. By electrophoresis experiments, it finds that the constructed sequencing library has similar bands (as shown in FIG. 3a, the electrophoresis path 5) to the DNA library constructed by a traditional method.

Embodiment 5

The method for constructing a plasma DNA sequencing library of the embodiment 5 is basically similar to the embodiment 1, and the difference is that, in the embodiment 5, the steps of end-filling and the dA-overhang are omitted; the extracted plasma DNA is directly ligated to the sequencing linker, and the single-strand sequencing linker is adopted to replace the double-strand sequencing linker in embodiment 1. The inventor finds that the plasma DNA library which satisfies the high-throughput sequencing requirements also can be obtained by adopting the single-strand sequencing linker instead of the double-strand sequencing linker, without performing the steps of end-filling and dA-overhang.

The Embodiments 1-5 of Sequencing the Plasma DNA Samples by using the Method According to the Embodiment 5 of the Disclosure are Shown as Below Step 1: extracting approximate 5 ng of the plasma DNA.

Step 2: respectively preparing the reaction mixture as shown in Table 14, incubating at 20 degrees centigrade for 60 min, so as to ligate linker to the DNA fragment; purifying and recycling the DNA samples by a Qiagen column and eluting the samples with 25 μl of sterile dH₂O or elution buffer. Alternatively, the T4 DNA ligase and the T4 RNA enzyme can have the proportional relations different from each specific embodiment.

Step 3: preparing the PCR reaction mixture as shown in Table 15, enriching the linker-modified DNA fragments by PCR; extracting the DNA samples by a Qiagen column, and eluting the samples with 25 μl of sterile dH₂O or elution buffer.

TABLE 15

| | |
|---|---|
| DNA | 23 μl |
| Phusion DNA polymerase (Phusion DNA polymerase mixture) | 25 μl |
| PCR primer mixture | 2 μl |
| Ultrapure water | 0 μl |
| Total volume | 50 μl |

Because of adopting the single-strand sequencing linker, the PCR reaction program is adjusted as follows: 72 degrees centigrade for 5 min—98 degrees centigrade for 30 s—4 circulations as follows: 98 degrees centigrade for 10 s, 30 degrees centigrade for 30 s, 72 degrees centigrade for 30 s—d. 98 degrees centigrade for 30 s—e. 16 circulations as follows: 98 degrees centigrade for 10 s, 65 degrees centigrade for 30 s, 72 degrees centigrade for 30 s—f. 72 degrees centigrade for 5 min—g. Maintaining at 4 degrees centigrade.

Step 4: quantifying and mixing the libraries: taking 1 μl of library to quantify by Qubit; an equal amount of mixing the sample libraries with different linkers in the same channel according to the channel arrangement; and taking 1 μl of library to quantify by Qubit again.

Step 5: sequencing by equipment: diluting the first-end sequencing primer, the tag primer and the second-end sequencing primer to 100 μM; operating the equipment according to the Illumina GAIIx operating instructions. Alternatively, the double-end sequencing can be performed, and the single-end sequencing also can be performed, the second-end sequencing primer can be omitted when performing the single-end sequencing.

Figure 3B:
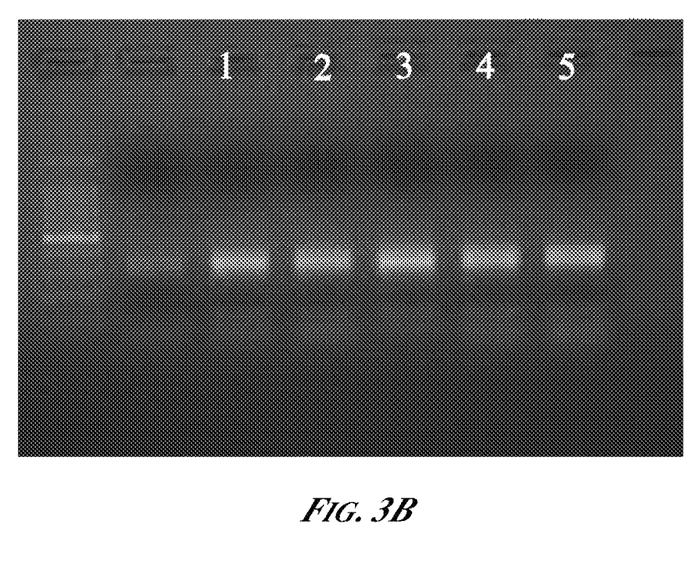
FIG. 3b shows the electrophoresis results of the plasma DNA sequencing library which is constructed according to the embodiment 5, wherein, the electrophoresis paths 1-5 are respectively the plasma sequencing libraries which are constructed according to the embodiments 1-5.

Results: the result of sequencing by equipment shows that the plasma DNA sequencing library constructed according to the embodiment 5 of the disclosure can satisfy the design requirements of the second-generation high-throughput sequencing. By electrophoresis experiments (as shown in FIG. 3b), it finds that the constructed sequencing library has similar bands to the DNA library which is constructed by a traditional method; and the similar electrophoresis bands can

TABLE 14

| Reagent | Embodiment 1 | Embodiment 2 | Embodiment 3 | Embodiment 4 | Embodiment 5 |
|---|---|---|---|---|---|
| Plasma DNA solution | 42 μl | 39 μl | 37 μl | 37 μl | 42 μl |
| Fast ligation reaction buffer (10X) | 5 μl | 5 μl | 5 μl | 5 μl | 5 μl |
| 5 μM single-strand DNA linker | 2 μl | 2 μl | 2 μl | 2 μl | 2 μl |
| T4 DNA ligase (NEB) | 0 μl | 2 μl | 4 μl | 5 μl | 1 μl |
| T4 RNA ligase (NEB) | 1 μl | 2 μl | 2 μl | 1 μl | 0 μl |
| Total volume | 50 μl | 50 μl | 50 μl | 50 μl | 50 μl | be obtained by adopting different proportions of T4 DNA ligase and T4 RMA enzymes.

In addition, the disclosure also provides a kit for constructing a DNA plasma sequencing library according to the embodiments 1-5 of the disclosure. According to different embodiments, the kit can include the enzyme for filling and repairing the plasma DNA end, the enzyme for overhanging adenine at the 3'-terminus of the DNA, including T4 DNA polymerase, Klenow enzyme, DNA polymerase, Taq enzyme and Klenow ex-(3'-5' exonuclease inactivity deletion); the enzyme for ligating the linker, including T4 DNA ligase, T4 RNA ligase, T7 DNA ligase, or the combinations thereof; the polymerase for performing the PCR amplification, including Phusion DNA polymerase and the like; and the buffers used for various enzymes; and the dNTP required by end-filling and PCR amplification, dATP required by dA-overhang, the double-strand sequencing linker or single-strand sequencing linker for the linker ligation, primers for the PCR amplification and the like.

As the disclosure finds that the 5'-terminus phosphorylation step can be omitted during the construction of a plasma DNA sequencing library, one important characteristic of the kit of the disclosure is that the reagent for performing 5'-terminus phosphorylation for the plasma DNA can be excluded.

In addition, as the disclosure adopts the Taq enzyme to perform dA-overhang without performing the 5'-terminus phosphorylation, the end-filling and dA-overhang can be performed in one reaction system, or the end-filling, dA-overhang and the ligation of the sequencing linker can be performed in one reaction system; thus, the kit of the disclosure may exclude the instruments and reagents for purifying after performing the end-filling, and/or the instruments and reagents for purifying after performing dA-overhang, consequently reducing the library construction cost, and simplifying the library construction flows.

If necessary, the kit of the disclosure further includes reagents and instruments for purifying end-filling products, reagents and instruments for purifying dA-overhang products, reagents and instruments for purifying ligation products of sequencing linker; and reagents and instruments for purifying PCR products and the like. The purification reagents can include the sterile dH$_2$O or elution buffer; purification devices can include purification columns or Qiagen columns. The purification reagent and instruments adopted in the disclosure are not limited by the specific reagents and instruments listed in this text, each of the purification reagents and instruments which are commonly used in the field can be applied in this disclosure according to the judgment of the technical staff.

It should be noted that, the above is only the preferred embodiment of the disclosure, but not intended to limit the scope of protection of the disclosure; for those skilled in the art, various changes and modifications can be made to the disclosure. For example, the dA-overhang step and the sequencing linker ligation step above also can be performed in one system, namely, the extracted plasma DNA can be performed with dA-overhang step, and the linker ligation step can be directly performed without performing the purification step. In addition, although the shown enzyme for ligating the sequencing linker is T4 DNA polymerase and/or T4 RNA polymerase, the T7 DNA polymerase, or the combination of the T7 DNA polymerase and the T4 DNA polymerase, and/or the combination of the T7 DNA polymerase and the T4 RNA polymerase also can be independently used. The reaction buffer, the PCR reaction flow and the like referred in the construction of the plasma DNA sequencing library also can be adjusted and changed correspondingly according to the specific requirements. Those skilled in the art should understand that any modifications, equivalent replacements, improvements and the like within the spirit and principle of the disclosure should fall within the scope of protection of the disclosure.

References

1. Lo Y M, et al. (1997) Presence of fetal DAN in maternal plasma and serum. Lancet, 350: 485-487.
2. Lo Y M, et al. (2007) Plasma placental RNA allelic ratio permits noninvasive prenatal chromosomal aneuploidy detection. Nat Med, 13: 218-223.
3. Tong Y K, et al. (2006) Noninvasive prenatal detection of fetal trisomy 18 by epigenetic allelic ratio analysis in maternal plasma: Theoretical and empirical considerations. Clin Chem, 52: 2194-2202.
4. Fan H C, Quake S R. (2007) Detection of aneuploidy with digital polymerase chain reaction. Anal Chem, 79: 7576-7579.
5. Lo Y M, et al. (2007) Digital PCR for molecular detection of fetal chromosomal aneuploidy. Proc Natl Acad Sci USA, 104: 13116-13121.
6. Bentley D R, et al. (2008) Accurate whole human genome sequencing using reversible terminator chemistry. Nature, 456: 53-59.
7. McKernan K J, et al. (2009) Sequence and structure variation in a human genome uncovered by short-read, massively parallel ligation sequencing using two-base encoding. Genome Research, 119: 1527-1541.
8. Harris T D, et al. (2008) Single-molecule DNA sequencing of a viral genome. Science, 320: 106-109.
9. Fan H C, et al. (2008) Noninvasive diagnosis of fetal aneuploidy by sequencing DNA from maternal blood. Proc Natl Acad Sci USA, 105: 16266-16271.
10. Chiu R W K, et al. (2008) Noninvasive prenatal diagnosis of fetal chromosomal aneuploidy by massively parallel genomic sequencing of DNA in maternal plasma. Proc Natl Acad Sci USA, 105: 20458-20463.
11. Chiu R W K, et al. (2010) Maternal plasma DNA analysis with massively parallel sequencing by ligation for noninvasive prenatal diagnosis of trisomy 21. Chin Chem, 56:459-463.

The invention claimed is:

1. A method for constructing a plasma Deoxyribonucleic acid (DNA) sequencing library, comprising:
    extracting a plasma DNA;
    ligating the plasma DNA with a sequencing linker, and purifying a ligation product;
    performing Polymerase Chain Reaction (PCR) amplification for a purified ligation product, purifying a PCR amplification product, and obtaining the plasma DNA sequencing library;
    wherein, the method does not comprise the step of performing 5'-terminus phosphorylation for the plasma DNA.

2. The method according to claim 1, wherein, ligating the plasma DNA with the sequencing linker is performed by adopting one or more ligases selected from the group consisting of: a T4 DNA ligase, a T4 Ribonucleic Acid (RNA) ligase and a T7 DNA ligase.

3. The method according to claim 1, wherein, the sequencing linker is a single-strand sequencing linker.

4. The method according to claim 1, wherein, the sequencing linker is a double-strand sequencing linker.

5. The method according to claim 4, wherein, after extracting the plasma DNA, and before ligating the plasma DNA with the sequencing linker, performing dA-overhang for the extracted plasma DNA, and purifying a plasma DNA with dA-overhang.

6. The method according to claim 5, wherein, adopting klenow ex-enzyme, or Taq enzyme, or the combination of klenow ex-enzyme and Taq enzyme for the dA-overhang.

7. The method according to claim 4, wherein, after extracting the plasma DNA, and before ligating the plasma DNA with the sequencing linker, performing end-filling and dA-overhang for the extracted plasma DNA.

8. The method according to claim 7, wherein, performing end-filling and dA-overhang in one reaction system, and then purifying an end-filled and dA-overhanged plasma DNA.

9. The method according to claim 8, wherein, adopting T4 DNA polymerase for the end-filling, adopting Taq enzyme for the dA-overhang.

10. The method according to claim 7, wherein, performing the end-filling and the dA-overhang, and the ligation between the plasma DNA and the sequencing linker in one reaction system.

11. The method according to claim 10, wherein, adopting the T4 DNA polymerase for the end-filling, adopting Taq enzyme for the dA-overhang.

* * * * *